United States Patent [19]

Lee

[11] Patent Number: 4,585,760

[45] Date of Patent: Apr. 29, 1986

[54] DIMETHYLFURANO HETEROCYCLIC ANALOGS OF DAUNOMYCIN

[75] Inventor: Ving J. Lee, Monsey, N.Y.

[73] Assignee: American Cyanamid Company, Stamford, Conn.

[21] Appl. No.: 284,017

[22] Filed: Jul. 16, 1981

[51] Int. Cl.$^4$ .................. A61K 31/70; C07H 15/24
[52] U.S. Cl. .................................... 514/34; 536/6.4; 549/457; 549/458; 549/214
[58] Field of Search .................. 536/18.1, 6.4, 34; 424/180

[56] References Cited

U.S. PATENT DOCUMENTS 4,125,607  11/1978  Arcamone et al. .................. 536/6.4
4,259,476  3/1981  Kende et al. ....................... 536/18.1

Primary Examiner—Johnnie R. Brown
Attorney, Agent, or Firm—M-E. M. Timbers

[57] ABSTRACT

Dimethyfurano analogs of daunomycin are described, including ($\pm$)-8$\alpha$-acetyl-6,7,8,9-tetrahydro-5,6$\beta$,8$\beta$,10-tetrahydroxy-1,3-dimethyl-anthra[2,3-c]-furan-4,11-dione-6-(3-amino-2,3-6-trideoxy-$\alpha$-L-lyxo-hexopyranoside), which are useful in the treatment of cancer in mammals, such as melanoma, squamous cell, myeloma and pranceatic.

8 Claims, No Drawings

DIMETHYLFURANO HETEROCYCLIC ANALOGS OF DAUNOMYCIN

BRIEF SUMMARY OF THE INVENTION

This invention relates to novel compounds which are dimethylfurano analogs of daunomycin, to precursor compounds useful in the synthesis of such analogs, and to processes of their therapeutic use as anti-tumor agents in mammals.

PRIOR ART

The compounds described herein are related to the compounds disclosed in U.S. Pat. Nos. 4,012,448 and 4,259,476.

DETAILED DESCRIPTION

The pharmacologically active compounds of this invention are represented by the formula

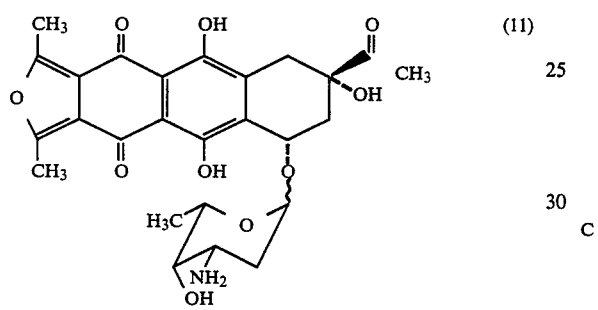

(11)

the individual α- and β-anomers, and pharmacologically acceptable salts and acid complexes, e.g., the hydrochloride complex, of the individual anomers and mixtures of any of said anomers, salts and/or complexes. The compound is named (±)-8α-acetyl-6,7,8,9-tetrahydro-5,6β,8β,10-tetrahydroxy-1,3-dimethyl-anthra[2,3-c]-furan-4,11-dione-6-(3-amino-2,3,6-trideoxy-α-L-lyxo-hexopyranoside), and its β-anomer. The α- and β-anomers are represented by formulas (11A) and (11B), respectively, as depicted hereinafter.

These compounds, and their pharmacologically acceptable salts and acid complexes, are useful as anti-tumor agents in mammals in a process of treatment, which process comprises administering to a mammal a therapeutically effective non-toxic amount of a compound represented by formula (11), or a mixture thereof, or a pharmaceutically acceptable salt or acid complex thereof.

The invention also comprises a plurality of novel compounds which are prepared as intermediates, or precursors, of the compounds of formula (11), as such intermediate compounds are described hereinafter in connection with processes of preparing compounds of formula (11).

Such processes are explained in conjunction with Flowcharts I, II and III, as well as in the various examples.

FLOWCHART I

STEP

A 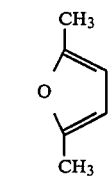 (12)

B CH₃O₂C(—C≡C—)CO₂CH₃ (13)

C 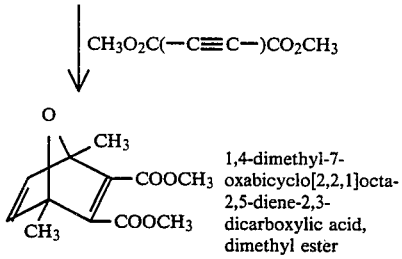 (14)

1,4-dimethyl-7-oxabicyclo[2,2,1]octa-2,5-diene-2,3-dicarboxylic acid, dimethyl ester H₂/Pd, heat D 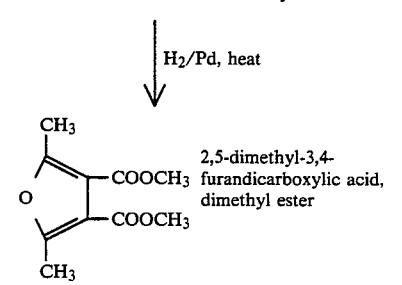 (15)

2,5-dimethyl-3,4-furandicarboxylic acid, dimethyl ester aq.NaOH

E 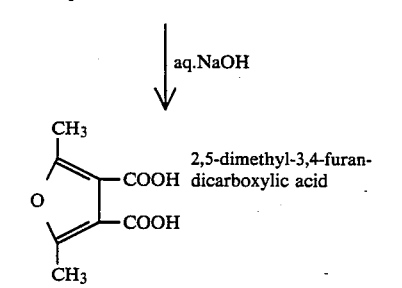 (16)

2,5-dimethyl-3,4-furandicarboxylic acid

SOCl₂

F 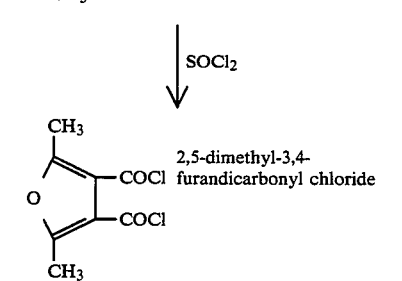 (17)

2,5-dimethyl-3,4-furandicarbonyl chloride 1,4-dimethoxy benzene and SnCl₄, in CH₂Cl₂; extraction; chromatography

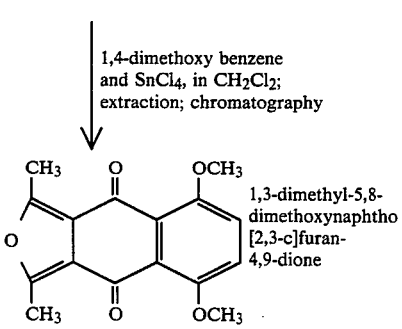 (18)

1,3-dimethyl-5,8-dimethoxynaphtho[2,3-c]furan-4,9-dione

AlCl₃/CH₂Cl₂

3

-continued
FLOWCHART I

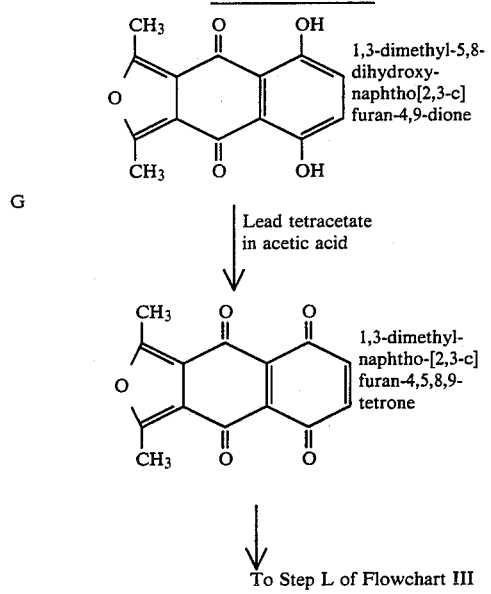

(19) 1,3-dimethyl-5,8-dihydroxy-naphtho[2,3-c]furan-4,9-dione

G ↓ Lead tetracetate in acetic acid

(20) 1,3-dimethyl-naphtho-[2,3-c]furan-4,5,8,9-tetrone

↓ To Step L of Flowchart III

FLOWCHART II

STEP

H   $HC\equiv C-CH(OH)-CH_3$

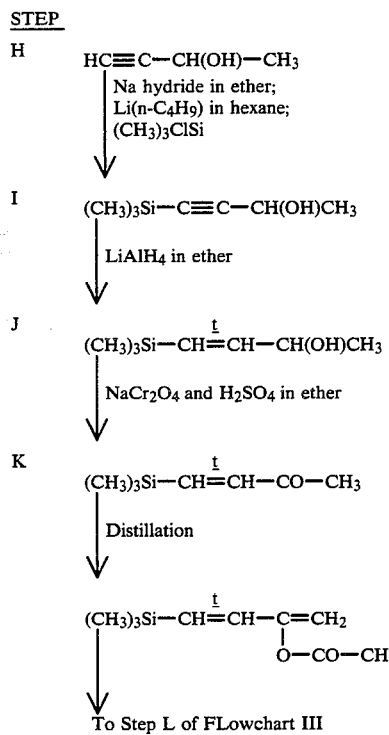

| Na hydride in ether;
| Li(n-$C_4H_9$) in hexane;
| $(CH_3)_3ClSi$
↓

I   $(CH_3)_3Si-C\equiv C-CH(OH)CH_3$ (22)

↓ $LiAlH_4$ in ether

J   $(CH_3)_3Si-\overset{t}{CH=CH}-CH(OH)CH_3$ (23)

↓ $NaCr_2O_4$ and $H_2SO_4$ in ether

K   $(CH_3)_3Si-\overset{t}{CH=CH}-CO-CH_3$ (24)

↓ Distillation $(CH_3)_3Si-\overset{t}{CH=CH}-\underset{O-CO-CH_3}{\overset{|}{C}}=CH_2$ (25) trans-4-(trimethylsilyl)-2-acetoxy-1,3-butadiene ↓ To Step L of Flowchart III

FLOWCHART III

STEP

The compound of formula (20) from Step G of Flowchart I and the compound of formula (25) from Step K of Flowchart II L   ↓ $CH_2Cl_2$, at 38–40° C.

4

-continued
FLOWCHART III

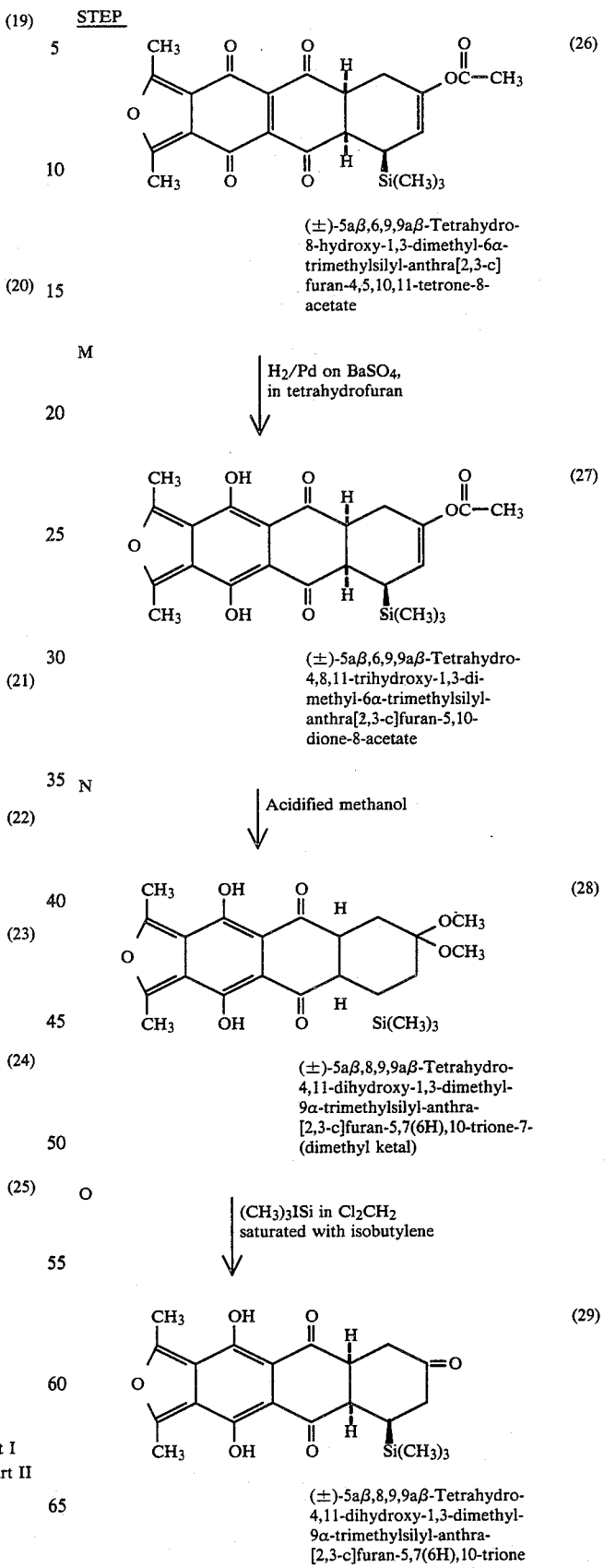

(26) (±)-5aβ,6,9,9aβ-Tetrahydro-8-hydroxy-1,3-dimethyl-6α-trimethylsilyl-anthra[2,3-c]furan-4,5,10,11-tetrone-8-acetate M ↓ $H_2$/Pd on $BaSO_4$, in tetrahydrofuran

(27) (±)-5aβ,6,9,9aβ-Tetrahydro-4,8,11-trihydroxy-1,3-dimethyl-6α-trimethylsilyl-anthra[2,3-c]furan-5,10-dione-8-acetate N ↓ Acidified methanol

(28) (±)-5aβ,8,9,9aβ-Tetrahydro-4,11-dihydroxy-1,3-dimethyl-9α-trimethylsilyl-anthra-[2,3-c]furan-5,7(6H),10-trione-7-(dimethyl ketal)

O ↓ $(CH_3)_3ISi$ in $Cl_2CH_2$ saturated with isobutylene

(29) (±)-5aβ,8,9,9aβ-Tetrahydro-4,11-dihydroxy-1,3-dimethyl-9α-trimethylsilyl-anthra-[2,3-c]furan-5,7(6H),10-trione

-continued
FLOWCHART III

STEP

P | HC≡CMgBr/THF; isopropenyl acetate and p-toluenesulfonic acid ↓

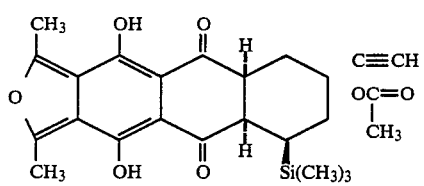

(30) (±)-8α-Ethynyl-5aβ,6,7,8,-9,9aβ-hexahydro-4,8β,11-trihydroxy-1,3-dimethyl-6α-trimethylsilyl-anthra-[2,3-c]furan-5,10-dione-8-acetate Q | Lead tetraacetate in acetic acid; potassium acetate in acetic acid ↓

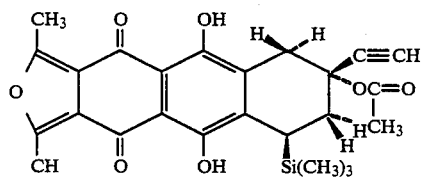

(31) (±)-8α-Ethynyl-6,7,8,9-tetrahydro-5,8β,10-trihydroxy-1,3-dimethyl-6α-trimethylsilyl-anthra-[2,3-c]furan-4,11-dione-8-acetate R | Lead tetraacetate in acetic acid; KF ↓

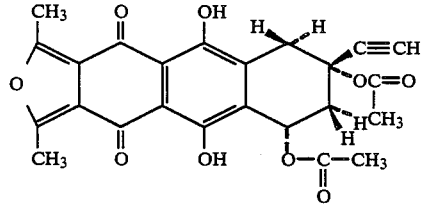

(32) (±)-8α-Ethynyl-6,7,8,9-tetrahydro-5,6β,8β,10-tetrahydroxy-1,3-dimethyl-anthra[2,3-c]furan-4,11-dione-6,8-diacetate S | Mercuric acetate and ethyl acetate in Cl₂CH₂/H₂S ↓

-continued
FLOWCHART III

STEP

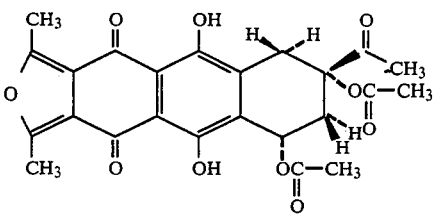

(33) (±)-8α-Acetyl-6,7,8,9-tetrahydro-5,6β,8β,10-tetrahydroxy-1,3-dimethyl-anthra[2,3-c]furan-4,11-dione-6,8-diacetate T | HCl/H₂O/methanol ↓

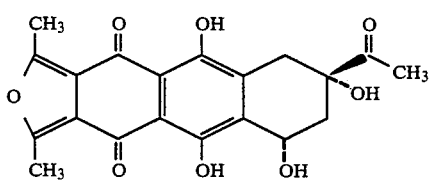

(34) (±)-8α-Acetyl-6,7,8,9-tetrahydro-5,6β,8β,10-tetrahydroxy-1,3-dimethyl-anthra[2,3-c]furan-4,11-dione U | Hg(CN)₂, HgBr₂; 2,3,6-trideoxy-4-(O—p-nitrobenzoyl)-3-trifluoroacetoamido-α-L-lyxo-hexopyranoside chloride; chromatography ↓

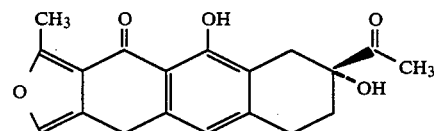

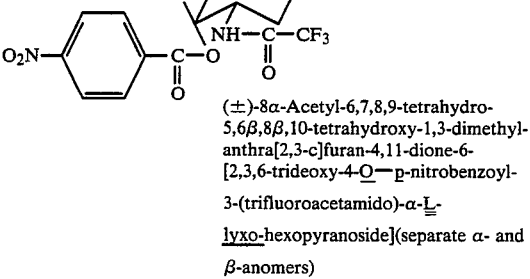

(35) (±)-8α-Acetyl-6,7,8,9-tetrahydro-5,6β,8β,10-tetrahydroxy-1,3-dimethyl-anthra[2,3-c]furan-4,11-dione-6-[2,3,6-trideoxy-4-O—p-nitrobenzoyl-3-(trifluoroacetamido)-α-L-lyxo-hexopyranoside](separate α- and β-anomers)

V | NaCl in NaOH; HCl ↓

-continued
FLOWCHART III

STEP

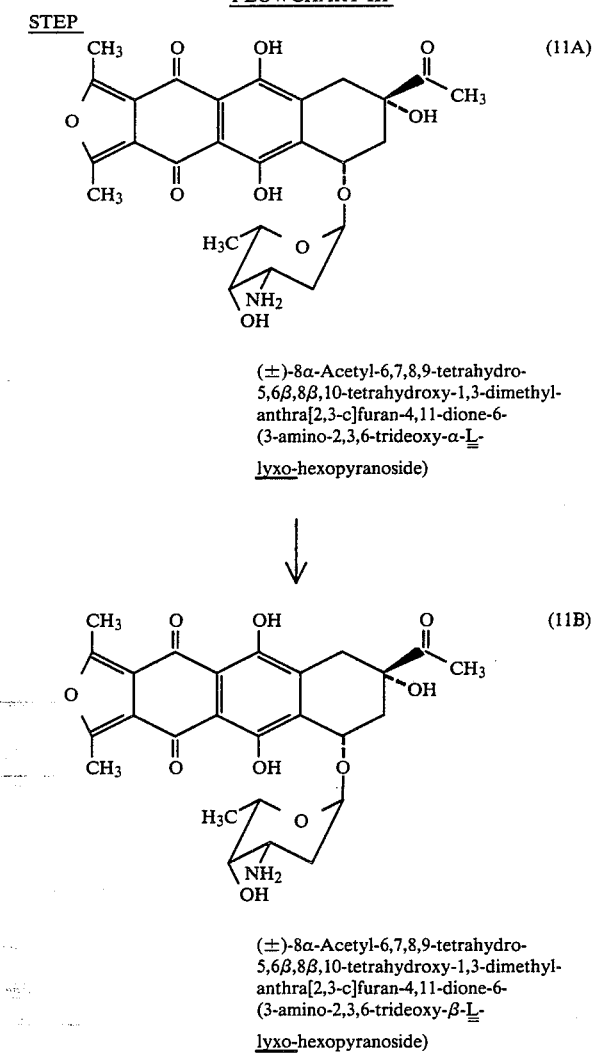

(11A)

(±)-8α-Acetyl-6,7,8,9-tetrahydro-
5,6β,8β,10-tetrahydroxy-1,3-dimethyl-
anthra[2,3-c]furan-4,11-dione-6-
(3-amino-2,3,6-trideoxy-α-L-
lyxo-hexopyranoside)

↓

(11B)

(±)-8α-Acetyl-6,7,8,9-tetrahydro-
5,6β,8β,10-tetrahydroxy-1,3-dimethyl-
anthra[2,3-c]furan-4,11-dione-6-
(3-amino-2,3,6-trideoxy-β-L-
lyxo-hexopyranoside)

In accordance with the Flowchart I, 2,5-dimethyl furan (formula 12) is reacted in step A with CH₃CO₂-(—C≡C—)CO₂CH₃ (formula 13) to produce 1,4-dimethyl-7-oxabicyclo[2,2,1]octa-2,5-diene-2,3-dicarboxylic acid, dimethyl ester (formula 14). The latter is catalytically hydrogenated in ethyl acetate (step B) to produce 2,5-dimethyl-3,4-furandicarboxylic acid, dimethyl ester (formula 15), which is treated with aqueous base at reflux for several hours and then acidified to produce 2,5-dimethyl-3,4-furandicarboxylic acid (formula 16). The latter is then treated (Step D) with thionyl chloride at reflux to produce 2,5-dimethyl-3,4-furandicarbonyl chloride (formula 17), which is then reacted in Step E with 1,4-dimethoxybenzene and anhydrous stannic chloride in dichloromethane at 0°-5° C. for several hours, and then acidified under an inert atmosphere. The product is extracted at 40°-45° C. in chloroform and chromatographed, to produce 1,3-dimethyl-5,8-dimethoxynaphtho[2,3-c]furan-4,9-dione (formula 18). Such dione (18) is then treated in step F with anhydrous aluminum chloride in dichloromethane at 40°-45° C. for several hours, acidified and extracted at 50°-55° C. into chloroform and crystallized from glacial acetic acid, to produce 1,3-dimethyl-5,8-dihydroxynaphtho[2,3-c]furan-4,9-dione (formula 19). The latter is then treated in step G with lead tetraacetate in acetic acid and extracted with dichloromethane, to produce 1,3-dimethylnaphtho-[2,3-c]furan-4,5,8,9-tetrone (formula 20).

Referring to Flowchart II, 3-butyn-2-ol (formula 21) is treated in step H with sodium hydride in ether at −20° C. and then with 2.0 n-butyllithium in hexane, followed by chlorotrimethylsilane, to produce (+)-4-trimethylsilyl-3-butyn-2-ol (formula 22), which is then reacted in step I with lithium aluminum hydride in ether at reflux for several hours, basified and distilled, to produce (±)-trans-4-(trimethylsilyl)-3-buten-2-ol (formula 23). The reaction in step J of (23) in ether with a mixture of sodium dichromate hydrate and sulfuric acid at <5° C. or below produces trans-4-(trimethylsilyl)-3-buten-2-one (formula 24), which upon distillation with selected solvents gives trans-4-(trimethylsilyl)-2-acetoxy-1,3-butadiene (formula 25).

Referring to Flowchart III, the 1,3-dimethylnaphtho[2,3-c]furan-4,5,8,9-tetrone (formula 20) and trans-4-(trimethylsilyl)-2-acetoxy-1,3-butadiene (formula 25) are, in step L, reacted in dichloromethane at 38°-40° C. for several hours, to produce (±)-5aβ,6,9,9aβ-tetrahydro-8-hydroxy-1,3-dimethyl-6α-trimethylsilyl-anthra[2,3-c]furan-4,5,10,11-tetrone-8-acetate (formula 26), which is then hydrogenated in step M with a noble metal catalyst in tetrahydrofuran, producing (±)-5aβ,6,9,9aβ-tetrahydro-4,8,11-trihydroxy-1,3-dimethyl-6α-trimethylsilyl-anthra[2,3-c]furan-5,10-dione-8-acetate (formula 27). In step N, the acetate 27 is suspended in methanol, acidified, refluxed several hours and chromatographed to produce (±)-5aβ,8,9,9aβ-tetrahydro-4,11-dihydroxy-1,3-dimethyl-9α-trimethylsilyl-anthra[2,3-c]furan-5,7(6H),10-trione-7-(dimethyl ketal) (formula 28). A cold solution of the dimethyl ketal (28) in isobutylene-saturated dichloromethane is treated with iodotrimethylsilane, quenched with aqueous sodium bicarbonate and chromatographed, to produce (±)-5aβ,8,9,9aβ-tetrahydro-4,11-dihydroxy-1,3-dimethyl-9α-trimethylsilyl-anthra[2,3-c]furan-5,7(6H),10-trione (formula 29). Such trione (29) is reacted in step P with ethynyl magnesium bromide in solvents, acetylene is bubbled into the mixture, citric acid is added and the product is chromatographed, to produce (±)-8α-ethynyl-5aβ,6,7,8,9,9aβ-hexahydro-4,8β,11-trihydroxy-1,3-dimethyl-6α-trimethylsilyl-anthra-[2,3-c]furan-5,10-dione-8-acetate (formula 30). Such acetate is then reacted in step Q with lead tetraacetate in glacial acetic acid, diluted with water, reacted with anhydrous potassium acetate in glacial acetic acid at 95° C., under an inert atmosphere for ½ hour and chromatographed, to produce (±)-8α-ethynyl-6,7,8,9-tetrahydro-5,8β,10-trihydroxy-1,3-dimethyl-6α-trimethylsilyl-anthra-[2,3-c]furan-4,11-dione-8-acetate (formula 31). The acetate (of formula 31) is reacted in step R with lead tetraacetate in glacial acetic acid for one hour, then with anhydrous potassium fluoride for several hours, diluted with dichloromethane and chromatographed, to produce (±)-8α-ethynyl-6,7,8,9-tetrahydro-5,6β,8β,10-tetrahydroxy-1,3-dimethyl-anthra[2,3-c]furan-4,11-dione-6,8-diacetate (formula 32). The diacetate (32) is reacted, in step S, with mercuric acetate in ethyl acetate-dichloromethane (5:1) at 40° C. for several hours, after which hydrogen sulfide is added, to produce (±)-8α-acetyl-6,7,8,9-tetrahydro-5,6β,8β,10-tetrahydroxy-1,3-dimethyl-anthra[2,3-c]furan-4,11-dione-6,8-diacetate (formula 33). In step T, a suspension of this diacetate (33) in hydrochloric acid-water-methanol (10:15:75) is refluxed under argon for several hours, to produce (±)-8α-acetyl-6,7,8,9-tetrahydro-5,6β,8β,10-tetrahydroxy-1,3-dimethyl-anthra[2,3-c]furan-4,11-dione (formula 34).

In step U, a mixture of the dione (34), 3A° molecular sieves, mercuric anhydride cyanide, mercuric bromide and dichloromethane is reacted with a chlorosugar, prepared from bubbling anhydrous hydrogen chloride into a dichloromethane suspension of 2,3,6-trideoxy-1,4-di-O-p-nitrobenzoyl-3-trifluoroacetamido-α-L-lyxohexapyranoside, by heating at 40° C. for several hours, to produce a mixture (shown as formula 35) of (±)-8α-acetyl-6,7,8,9-tetrahydro-5,6β,8β,10-tetrahydroxy-1,3-dimethyl-anthra[2,3-c]-furan-4,11-dione-6-[2,3,6-trideoxy-4-O-p-nitrobenzoyl-3-(trifluoroacetamido)-α-L-lyxo-hexopyranoside] and the corresponding β-anomer. By means of chromatography, the mixture of formula 35 may be separated into the α-anomer and the β-anomer.

As an additional optional step (not shown on Flowchart III), a solution of the α-anomer of formula 35 in tetrahydrofuran at 0° C. under an inert atmosphere is basified, then acidified, extracted into chloroform to produce the free base of formula 11A, and then treated with ethanolic hydrogen chloride, to produce the hydrochloride complex of (±)-8α-acetyl-6,7,8,9-tetrahydro-5,6β,8β10-tetrahydroxy-1,3-dimethyl-anthra-[2,3-c]furan-4,11-dione-6-(3-amino-2,3,6-trideoxy-α-L-lyxo-hexopyranoside).

The β-anomer of formula 35 is converted to the free base of formula 11B, and then to the hydrochloride complex, in the same manner.

The novel compounds of the present invention possess the property of inhibiting the growth of transplanted mouse tumors as established by the following test.

MELANOTIC MELANOMA B16

The animals used were C57BC/6 mice, all of the same sex, weighing a minimum of 17 g. and all within a 3 g. weight range. There were normally 10 animals per test group. A one-gram portion of melanotic melanoma B16 tumor was homogenized in 10 ml. of cold balanced salt solution and a 0.5 ml. aliquot of the homogenate was implanted intra-peritoneally into each of the test mice. The test compounds were administered intraperitoneally on days one, five and nine (relative to tumor inoculation) at various doses. The animals were weighed and the survivors were recorded on a regular basis for 60 days. The median survival time and the ratio of survival time for treated (T)/control (C) animals was calculated. The positive control compound is Daunomycin given over a dose range of 0.07–5.0 mg./kg. The results of this test with a representative compound of the present invention appear in Table I. The criterion for efficacy is that 100 times the T/C ratio equal or exceed 125%.

TABLE I

| Compound | Melanotic Melanoma B16 | | |
|---|---|---|---|
| | Dose (mg./kg.) | Median Survival (Days) | T/C × 100 (Percent) |
| (±)-8α-Acetyl-6,7,8,9-tetrahydro-5,6β,8β,10-tetrahydroxy-1,3-dimethyl-anthra-[2,3-c]-furan-4,11-dione-6-(3-amino-2,3,6-trideoxy-α-L-lyxo-hexopyranoside)hydrochloride | 5.0 | 33.0 | 157 |
| | 2.5 | 29.5 | 140 |
| | 1.25 | 26.5 | 126 |
| | 0.62 | 25.0 | 119 |
| | 0.31 | 24.0 | 114 |

TABLE I-continued

| Compound | Melanotic Melanoma B16 | | |
|---|---|---|---|
| | Dose (mg./kg.) | Median Survival (Days) | T/C × 100 (Percent) |
| Control | 0 | 21.0 | — |
| Daunomycin | 5.0 | 17.5 | 83 |
| | 2.5 | 41.0 | 195 |
| | 1.25 | 43.0 | 205 |
| | 0.62 | 30.0 | 143 |
| | 0.31 | 28.5 | 136 |
| | 0.15 | 28.5 | 136 |
| | 0.07 | 22.0 | 105 |
| Adriamycin | 10.0 | 59.5 | 283 |
| | 5.0 | >60.0 | >286 |
| | 2.5 | 38.5 | 181 |
| | 1.2 | >60.0 | >286 |
| | 0.62 | >60.0 | >286 |
| | 0.31 | >60.0 | >286 |
| | 0.15 | 37.5 | 179 |

The hydrochloride complex of the compound of formula 11A was tested for activity against various tumors by the stem cell assay system described by S. Salmon, et al., "Quantification of Differential Sensitivity of Human Tumor Stem Cells to Anticancer Drugs," New England J. of Medicine, Vol. 298, p. 1321 (1978), with the following results:

| Tumor Type | Percent kill with | |
|---|---|---|
| | Compound of Formula 11A, HCl Complex | Adriamycin |
| ovarian | 0 | 0 |
| melanoma | 31 | 0 |
| neuroblastoma | 43 | 62 |
| melanoma | 31 | 0 |
| lung, squamous | 30 | 14 |
| myeloma | 53 | 83 |
| pancreas | 51 | 66 |
| mesothelioma | 0 | 32 |
| leukemia | 43 | 53 |
| adeno (origin not defined) | 88 | 0 |
| ovarian | 35 | 24 |
| melanoma | 0 | 0 |
| breast | 17 | 60 |

A plurality of references to the same type of tumor indicates clones of tumors from different persons, or from different locations in the same person.

The pharmaceutical compositions can be in forms suitable for injectable use, which forms include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active ingredient or ingredients in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmacetically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the present compositions is contemplated. Supplementary active ingredients can also be incorporated into the inventive compositions.

It is especially advantageous to formulate compositions in dosage unit form for ease of administration and uniformity of dosage. Dosage unit form as used in the specification and claims herein refers to physically discrete units suited as unitary dosages for the animal subjects to be treated, each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as disclosed in detail in this specification.

The dosage of the principal active ingredient for the treatment of the indicated conditions depends upon the age, weight and condition of the subject being treated; the particular condition and its severity; the particular form of the active ingredient and the route of administration. A daily dose of from about one to about 100 mg./kg. of body weight given singly or in divided doses of up to 5 times a day embraces the effective range for the treatment of most conditions for which the novel compounds are effective and substantially non-toxic. For a 75 kg. subject, this translates into between about 75 and about 7500 mg./day. If the dosage is divided, for example, into 3 individual dosages, these will range from about 25 to about 2500 mg. of the active ingredient. The preferred range is from 2 to about 50 mg./kg. of body weight/day with about 2 to about 30 mg./kg./day being more preferred.

The principal active ingredient is compounded for convenient and effective administration in effective amounts with a suitable pharmaceutically-acceptable carrier in dosage unit form as hereinbefore disclosed. A unit dosage form can, for example, contain the principal active ingredient in amounts ranging from about 0.1 to about 400 mg., with from about one to about 30 mg. being preferred. Expressed in proportions, the active ingredient is generally present in from about 0.1 to about 400 mg./ml. of carrier. In the case of compositions containing supplementary active ingredients, the dosages are determined by reference to the usual dose and manner of administration of the said ingredients.

Regression and palliation of cancers are attained, for example, using intraperitoneal administration. A single intravenous dosage or repeated daily dosage can be administered. Daily dosages up to about 5 or 10 days are often sufficient. It is also possible to dispense one daily dosage or one dose on alternate or less frequent days. As can be seen from the dosage regimens, the amount of principal active ingredient administrated is a sufficient amount to aid regression and palliation of the leukemia or the like, in the absence of excessive deleterious side effects of a cytotoxic nature to the hosts harboring the cancer. As used herein, cancer means blood malignancies such as leukemia, as well as other solid and nonsolid malignancies such as the melanocarcinomas, lung carcinomas and mammary tumors. By regression and palliation is meant arresting or retarding the growth of the tumor or other manifestation of the disease compared to the course of the disease in the absence of treatment.

EXAMPLE 1

1,4-Dimethyl-7-oxabicyclo[2,2,1]octa-2,5-diene-2,3-dicarboxylic acid, dimethyl ester A mixture of 144.5 g. of 2,5-dimethylfuran and 200 g. of dimethyl acetylenedicarboxylate was heated on a steam bath for 10 hours. Distillation through a Vigreux column gave 268 g. (colorless) of the compound of formula (14): b.p. 92°–94° C. (0.2 mm Hg.); IR (Neat) 1720, 1640, 1565, 1440, 1385, 1310 and 1260 cm$^{-1}$; $^1$H NMR (CDCl$_3$, 90 MHz) $\delta$ 1.80 (s, 6H, CH$_3$), 3.77 (s, 6H, OCH$_3$), and 6.86 (s,2H, =CH).

EXAMPLE 2

2,5-Dimethyl-3,4-furandicarboxylic acid, dimethyl ester

A mixture of 238.1 g. of 1,4-dimethyl-7-oxabicyclo-[2,2,1]octa-2,5-diene-2,3-dicarboxylic acid dimethyl ester (formula 14), 5.0 g. of 5% palladium on calcium carbonate catalyst (poisoned with lead) and one liter of ethyl acetate was hydrogenated in a Parr apparatus. Removal of the catalyst and concentration in vacuo gave the crude intermediate which was then heated with stirring to 240°–250° C., under argon for 4 hours and then distilled, giving 184.0 g. of the crystalline compound of formula (15): b.p. 264°–265° C. (745 mm Hg); IR (KBr) 1710, 1600, 1445, 1233–1215, and 1085 cm$^{-1}$; $^1$H NMR (CDCl$_3$, 90 MHz) $\delta$ 2.44 (s, 6H, CH$_3$) and 3.84 (s,6H, OCH$_3$).

EXAMPLE 3

2,5-Dimethyl-3,4-furandicarboxylic acid

A mixture of 385 g. of 2,5-dimethyl-3,4,-furandicarboxylic acid, dimethyl ester (formula 15), 200 g. of sodium hydroxide and one liter of water was heated at reflux for 18 hours, then cooled, filtered and acidified with 12N hydrochloric acid. The resulting solid was collected, washed with water, dried and crystallized from acetone-hexane, giving 290 g. of the product (formula 16) as a while solid: m.p. 232°–235° C.; IR (KBr) 2960, 1685, 1630, 1600, 1575, 1465, 1370, 1265, 1210, 775 and 700 cm$^{-1}$; $^1$H NMR (CD$_3$COCD$_3$, 90 MHz) δ 2.60 (s, 6H, CH$_3$) and 6.86 (bs, 2H, COOH).

EXAMPLE 4

2,5-Dimethyl-3,4-furandicarbonyl chloride

A mixture of 28.0 g. of 2,5-dimethyl-3,4-furandicarboxylic acid (formula 16) and 100 ml. of thionyl chloride was heated at reflux for 6 hours and concentrated *in vacuo*. The residue was distilled, giving 31.0 g. of the compound having a faint yellow color of formula (17): b.p. 119°–120° C. (1 mm Hg); IR (Neat) 1760, 1565, 1275, 920 and 845 cm$^{-1}$; $^1$H NMR (CDCl$_3$, 90 MHz) δ 2.58 (s, 6H, CH$_3$).

EXAMPLE 5

1,3-Dimethyl-5,8-dimethoxynaphtho[2,3-c]furan-4,9-dione

A stirred solution of 82.9 g. of 1,4-dimethoxy-benzene, 287 g. of anhydrous stannic chloride and 800 ml. of anhydrous dichloromethane at 0°–5° C. was treated dropwise over one hour with a solution of 110.6 g. of 2,5-dimethyl-3,4-furandicarbonyl chloride (formula 17) in 125 ml. of anhydrous dichloromethane. After 2 hours at 0°–5° C., the suspension was poured, under argon, into 2 liters of vigorously stirred, cold (0° C.) 2N hydrochloric acid. The dichloromethane was allowed to evaporate and the solid was collected and washed successively with 4 liters of water, 3 liters of 0.5N sodium hydroxide and finally water. The crude product was dried, then extracted for 36 hours in a Soxhlet apparatus with 1.5 liters of chloroform. The warm (40°–45° C.) extract was percolated, under slight pressure, through a 65×450 mm. column containing neutral alumina. The column was eluted with 3 liters of chloroform and 2 liters of ether. After concentration *in vacuo*, the residue was crystallized from 2-methoxyethanol, giving 125.0 g. of the compound of formula (18) as yellow plates: m.p. 227°–228° C.; IR (KBr) 1670, 1560–1600, 1266, 1220, 1278, 1055, 973, 835, 770 and 723 cm$^{-1}$; $^1$H NMR (CDCl$_3$, 100 MHz) δ 2.66 (s, 6H, CH$_3$), 3.96 (s, 6H, OCH$_3$), and 7.27 (s, 2H, aromatic CH). Calc'd. for C$_{16}$H$_{14}$O$_5$: C, 67.13; H, 4.93; O, 27.94. Found: C, 67.19; H, 5.05.

EXAMPLE 6

1,3-Dimethyl-5,8-dihydroxynaphtho[2,3-c]furan-4,9-dione

A stirred suspension of 71.5 g. of 1,3-dimethyl-5,8-dimethoxynaphtho[2,3-c]furan-4,9-dione (formula 18) in 1.5 liters of dichloromethane was treated portionwise with 86.7 g. of anhydrous aluminum chloride. After 28 hours at 40°–45° C., the suspension was carefully poured into 2 liters of cold 2N hydrochloric acid with vigorous stirring and then heated to 50° C. on a steam bath. The solid was collected, washed with water, dried in vacuo, then extracted in a Soxhlet apparatus with 1.5 liters of chloroform. The warm (50°–55° C.) extract was filtered through a 90×150 mm. bed of hydrous magnesium silicate, eluting with chloroform. The chloroform was evaporated and the residue was crystallized from 1.5 liters of glacial acetic acid, giving 54.9 g. of the compound of formula (19) as reddish-orange needles: m.p. 255°–256° C.; IR (KBr) 1650, 1620–1580, 1470, 1360, 1280, 1215, 1150, 1055, 815 and 715 cm$^{-1}$; $^1$H NMR (CDCl$_3$, 100 MHz) δ 2.63 (s, 6H, CH$_3$), 7.12 (s, 2H, aromatic CH), and 12.92 (s, 2H, phenolic OH).

EXAMPLE 7

1,3-Dimethylnaphtho[2,3-c]furan-4,5,8,9-tetrone

A mixture of 3.3 g. of 1,3-dimethyl-5,8-dihydroxynaphtho[2,3-c]furan-4,9-dione (formula 19), 12.0 g. of 94% lead tetraacetate, 2 ml. of dichloromethane and 50 ml. of glacial acetic acid was ground in a mortar. This mixture was poured into 200 ml. of water and the precipitate collected and washed with water. This solid was dried, then extracted in a Soxhlet apparatus with dichloromethane for 18 hours. Concentration of the extract and boiling the residue with acetone gave 2.9 g. of the compound of formula (20) as reddish-brown microneedles: m.p. >270° C.; IR (KBr) 1700, 1650, 1605,, 1430, 1285, 1220, 1110, 863 and 802 cm$^{-1}$; $^1$H NMR (CDCl$_3$, 100 MHz) δ 2.65 (s, 6H, CH$_3$) and 6.84 (s, 2H, =CH). Calc'd. for C$_{14}$H$_8$O$_5$: C, 65.63; H, 3.15; O, 31.22. Found: C, 65.84; H, 3.33.

EXAMPLE 8

(±)-4-Trimethylsilyl-3-butyn-2-ol

A cold (−20° C.) suspension of 58.0 g. of sodium hydride in 3.5 liters of anhydrous ether was treated, dropwise, over one hour with 140.9 g. of (±)-3-butyn-2-ol (formula 21). This suspension was then treated at −20° C. with 1050 ml. of 2.0M n-butyllithium in hexane. After 2 hours at −20° C. this suspension was then treated over a one hour period with 488.7 g. of chlorotrimethylsilane. This suspension was heated to 50° C., about 2 liters of solvent was distilled off, then the mixture was cooled and diluted with one liter of water, 250 ml. of 32% hydrochloric acid and 500 ml. of methanol. The mixture was stirred for 24 hours, then extracted with ether. The ether layer was washed successively with water and brine, and then dried over anhydrous magnesium sulfate. Solvents were evaporated in vacuo and the crude product was distilled, giving 256.0 g. of the compound of formula (22): b.p. 81°–82° C. (20 mm Hg); IR (Neat) 3440, 2200, 1250,, 1115, 1045, 945, 865, 838 and 755 cm$^{-1}$; $^1$H NMR (CDCl$_3$, 90 MHz) δ 0.15 (s, 9H, (CH$_3$)$_3$Si), 1.42 (d, 3H, J=7.0 Hz, CH$_3$CH), 1.92 (s, 1H, OH) and 4.50 (q, 1H, CHOH).

EXAMPLE 9

(±)-trans-4-Trimethylsilyl-3-buten-2-ol

A mixture of 28.5 g. of lithium aluminum hydride in 1.6 liters of anhydrous ether was treated with 142.2 g. of (±)-4-trimethylsilyl-3-butyn-2-ol (formula 22). The mixture was refluxed for 40 hours then treated dropwise in succession with 28.5 ml. of water, 28.5 ml. of 5% sodium hydroxide and 85.5 ml. of water. The solid was separated by filtration, washed with ether and the filtrates were dried and then solvent was removed by distillation in a Vigreux column at 745 mm. The residue was then distilled, giving 130 g. of the compound of formula (23): b.p. 63°–64° C. (20 mm Hg); IR (Neat) 3340, 1610, 1245, 1100, 1055, 860, 835 and 755 cm$^{-1}$; $^1$H NMR (CDCl$_3$, 90 MHz) δ 0.14 (s, 9H, (CH$_3$)$_3$Si), 1.26 (d, 3H, J=6.2 Hz, CH$_3$CH), 1.75 (bs, 1H, OH), 4.40 (m, 1H, CHC=), 5.62 (d, 1H, J=19.0 Hz, 4-H), and 6.30 (dd, 1H, J=19.0 and 6.2 Hz, 3-H).

EXAMPLE 10 trans-4-Trimethylsilyl-3-buten-2one

A stirred, cold (−25° C.) solution of 63.0 g. of (±)-trans-4-trimethylsilyl-3-buten-2-ol (formula 23) in one liter of ether was treated, dropwise, with a solution of 51.4 g. of sodium dichromate hydrate, 47.0 ml. of concentrated sulfuric acid and 300 ml. of water. The addition was maintained so that the internal temperature did not exceed 5° C. This mixture was stirred overnight at 26° C. and extracted with ether. The ether extracts were washed with water, then with brine, and dried over magnesium sulfate. The solvent and product were distilled through a Vigreux column, giving 51.0 g. of the compound of formula (24): b.p. 164°–167° C. (740 mm Hg.); IR (Neat) 1720, 1700, 1680, 1250, 1000, 860 and 840 cm$^{-1}$; $^1$H NMR (CDCl$_3$, 90 MHz) δ 0.12 (s, 9H, (CH$_3$)$_3$Si), 2.25 (s, 3H, CH$_3$CO), 6.36 (d, 1H, J=19.0 Hz, 3-H) and 7.03 (d, 1H, J=19.0 Hz, 4-H).

EXAMPLE 11 trans-4-Trimethylsilyl-2-acetoxy-1,3-butadiene

A mixture of 7.0 g. of p-toluenesulfonic acid monohydrate and 500 ml. of benzene was distilled through a Vigreux column equipped with a Dean-Stark trap. Approximately 350 ml. of distillate was removed and 500 ml. of distilled isopropenyl acetate was added. The distillation was resumed until the distillate reached 92° C. The distillation pot was cooled to about 50° C. and 100.0 g. of trans-4-trimethylsilyl-3-buten-2-one (formula 24) was added. Slow distillation (85°–87° C.) was resumed for 18 hours. The residue was flash distilled at one mm Hg. into a cold (−70° C.) receiver. This material was redistilled through a glass helices-packed (20×240 mm) column, giving 65.0 g. of the compound of formula (25): b.p. 78°–70° C. (15–20 mm Hg); IR (Neat) 1765, 1640, 1585, 1370, 1245, 1210–1175, 1020, 980, 965, 917 and 880–830 cm$^{-1}$; $^1$H NMR (CDCl$_3$, 90 MHz) δ 0.09 (s, 9H, (CH$_3$)$_3$Si), 2.24 (s, 3H, CH$_3$CO), 4.93 (d, 1H, J=1.5 Hz, 1-H$_A$), 5.03 (d, 1H, J=1.5 Hz, 1-H$_B$), 5.95 (d, 1H, J=18.8 Hz, 4-H) and 6.37 (d, 1H, J=18.8 Hz, 3-H).

EXAMPLE 12

(±-5aβ,6,9,9aβ-Tetrahydro-8-hydroxy-1,3-dimethyl-6α-trimethylsilyl-anthra[2,3-c]furan-4,5,10,11-tetrone-8-acetate A mixture of 15.2 g. of 1,3-dimethylnaphtho[2,3-c]-furan-4,5,8,9-tetrone (formula 20), 14.8 g. of trans-4-trimethylsilyl-2-acetoxy-1,3-butadiene (formula 25) and 150 ml. of dichloromethane was stirred at 38°–40° C. for 48 hours and concentrated in vacuo. The oily residue was triturated with ether and the solid was collected and dried in vacuo, giving 10.0 g. of the light orange compound of formula (26) that was >95% pure according to $^1$H NMR (90 MHz): m.p. 188°–189° C.; IR (KBr) 1765, 1715, 1665, 1605, 1430, 1370, 1275–1200, 1125 and 870–840 cm$^{-1}$; $^1$H NMR (CDCl$_3$, 80 MHz) δ 0.17 (s, 9H, (CH$_3$)$_3$Si), 1.93 (m, 1H, 6-H), 2.09 (s, 3H, CH$_3$CO), 2.40–2.80 (m, 2H, 9-H$_2$), 2.63 (s, 6H, CH$_3$), 3.40 (m, 1H, 9a-H), 3.71 (dd, 1H, J=4.9 Hz, 5a-H) and 5.47 (m, 1H, 7-H). Calc'd. for C$_{23}$H$_{24}$O$_7$Si: C, 62.71; H, 5.49; O, 25.42; Si, 6.37. Found: C, 62.04; H, 5.33.

EXAMPLE 13

(±)-5aβ,6,9,9aβ-Tetrahydro-4,8,11-trihydroxy-1,3-dimethyl-6α-trimethylsilyl-anthra[2,3-c]furan-5,10-dione-8-acetate A mixture of 20.0 g. of (±)-5aβ,6,9,9aβ-tetrahydro-8-hydroxy-1,3-dimethyl-6α-trimethylsilyl-anthra[2,3-c]-furan-4,5,10,11-tetrone-8-acetate (formula 26), 2.0 g. of 5% palladium on barium sulfate catalyst and 400 ml. of tetrahydrofuran was hydrogenated in a Parr apparatus. The catalyst was filtered off and the filtrate concentrated, then taken up in 250 ml. of tetrahydrofuran, cooled overnight at −20° C. and filtered. The filtrate was percolated through a 50×83 mm bed of hydrated magnesium silicate and eluted with chloroform, giving 17.5 g. of the compound of formula (27) as an orange solid, m.p. 160°–170° C. An analytical sample was obtained by crystallization (2X) from 2-butanone-methanol (1:3); m.p. 171°–172° C.; IR (KBr) 1760, 1630, 1610, 1585, 1545, 1415, 1250, 1215, 1125 and 840 cm$^{-1}$; $^1$H NMR (CDCl$_3$, 80 MHz) δ 0.13 (s, 9H, Si(CH$_3$)$_3$), 1.92 (m, 1H, 6-H), 2.10 (s, 3H, CH$_3$CO), 2.45 (m, 2H, 9-H$_2$), 2.75 (s, 6H, CH$_3$), 3.10 (m, 1H, 9a-H), 3.37 (dd, 1H, J=4.9 and 4.6 Hz, 5a-H), 5.49 (bd, 1H, 7-H), 14.23 (s, 1H, phenolic OH), and 14.39 (s, 1H, phenolic OH); mass spectrum (70 ev) m/e (relative intensity) 442 (M$^+$, 20), 427 (10), 400 (12), 399 (20) and 258 (58). Calc'd. for C$_{23}$H$_{26}$O$_7$Si: C, 62.43; H, 5.92; O, 25.30; Si, 6.35. Found: C, 62.09; H, 5.83.

EXAMPLE 14

(±)-5aβ,8,9,9β-Tetrahydro-4,11-dihydroxy-1,3-dimethyl-9α-trimethylsilyl-anthra[2,3-c]furan-5,7(6H), 10-trione-7-(dimethyl ketal)

A suspension of 6.7 g. of (±)-5aβ,6,9,9aβ-tetrahydro-4,8,11-trihydroxy-1,3-dimethyl-6α-trimethylsilyl-anthra[2,3-c]furan-5,10-dione-8-acetate (formula 27), 150 ml. of methanol and one ml. of 38% hydrochloric acid was heated at reflux for 3 hours and then concentrated in vacuo. The residue was dried azeotropically with 250 ml. of benzene, then taken up in chloroform and percolated through a 120×70 mm bed of hydrated magnesium silicate, eluting with chloroform. The chloroform solution was taken up in 250 ml. of ether and chilled (0° C.) overnight, giving 4.9 g. of the compound of formula (28) as a yellowish-orange solid, m.p. 186°–188° C. An analytical sample, m.p. 188.5°–189° C., was obtained by crystallization from benzene-ether; IR (KBr) 1620, 1580, 1535, 1430, 1290–1245, 1175, 1125, 1050, 870–850 and 840 cm$^{-1}$, $^1$H NMR (CDCl$_3$, 80 MHz) δ 0.12 (s, 9H, (CH$_3$)$_3$Si), 0.95 (dt, 1H, J=13.0 and 4.5 Hz, 9-H), 1.33 (dd, 2H, J=13.0 and 5.2 Hz, 8-H$_2$), 1.75–2.25 (m, 2H, 6-H$_2$), 2.76 (s, 6H, CH$_3$), 2.85 (m, 1H, 9a-H), 3.10 (m, 1H, 5a-H), 3.19 (s, 3H, OCH$_3$), 3.20 (s, 3H, OCH$_3$), 14.59 (s, 1H, phenolic OH) and 14.79 (s, 1H, phenolic OH); mass spectrum (70 ev) m/e (relative intensity) 446 (M$^+$, 5), 414 (15), 309 (28) and 258 (100). Calc'd. for C$_{23}$H$_{30}$O$_7$Si: C, 61.86; H, 6.77; O, 25.08; Si, 6.29. Found: C, 61.91; H, 6.66.

EXAMPLE 15

(±)-5aβ,8,9,9aβ-Tetrahydro-4,11-dihydroxy-1,3-dimethyl-9α-trimethylsilyl-anthra[2,3-c]furan-5,7(6H),10-trione A cold (0° C.) solution of 446 mg. of (±)-5aβ,8,9,9aβ-tetrahydro-4,11-dihydroxy-1,3-dimethyl-9α-trimethylsilyl-anthra[2,3-c]furan-5,7(6H),10-trione-7-(dimethyl ketal) (formula 28) in 50 ml. of isobutylene saturated dichloromethane was treated with 300 mg. of iodotrimethylsilane. After 30 minutes the reaction was quenched with 100 ml. of 5% sodium bicarbonate solution and extracted with dichloromethane. The extracts were washed with water, then with brine and dried over sodium sulfate. Removal of solvent in vacuo gave an orange foam. This foam was purified on preparative tlc plates (silica gel GF$_{254}$—2×1 mm×20 cm×20 cm, benzene) and the major yellow-orange band extracted to give 301 mg. of the compound of formula (29) as a foam: IR (KBr) 1730, 1650, 1425, 1170 and 850 cm$^{-1}$; $^1$H NMR (CDCl$_3$, 90 MHz) δ 0.13 (s, 9H, (CH$_3$)$_3$Si), 1.20 (ddd, 1H, J=13.8, 4.5 and 3.80 Hz, 9-H), 2.23 (m, 2H, J=13.8 and 3.8 Hz, 8-H$_2$), 2.62 (m, 2H, J=16.0 and 4.7 Hz, 6-H$_2$), 2.68 (s, 6H, CH$_3$), 3.10 (dd, 1H, J=5.3 and 4.2 Hz, 9a-H), 3.30 (m, 1H, 5a-H), 14.38 (s, 1H, phenolic OH) and 14.45 (s, 1H, phenolic OH).Calc'd. for C$_{21}$H$_{24}$O$_6$Si: C, 62.98; H, 6.04; O, 23.97; Si, 7.01. Found: C, 62.78; H, 6.10; Si, 6.98.

EXAMPLE 16

(±)-8α-Ethynyl-5aβ,6,7,8,9,9aβ-hexahydro-4,8β,11-trihydroxy-1,3-dimethyl-6α-trimethylsilyl-anthra-[2,3-c]furan-5,10-dione-8-acetate A cold solution of ethynyl magnesium bromide (prepared from the reaction of 40 ml. of 2.94M ethyl magnesium bromide in ether with purified gaseous acetylene in 450 ml. of anhydrous tetrahydrofuran) in 500 ml. of anhydrous tetrahydrofuran was treated with a solution of 6.05 g. of (±)-5aβ,8,9,9aβ-tetrahydro-4,11-dihydroxy-1,3-dimethyl-9α-trimethylsilyl-anthra-[2,3-c]furan-5,7(6H),10-trione (formula 29) in 50 ml. of dry dichloromethane. Acetylene was bubbled through the solution for 2 hours, then 200 ml. of 5% citric acid solution was added and the mixture extracted with ether. The extracts were washed with water, then with brine and dried over sodium sulfate, giving an oil after removal of solvents in vacuo. This oil was chromatographed on a dry column of silicic acid (50×800 mm, benzene) to give a dark foam. A mixture of this foam, 25 ml. of distilled isopropenyl acetate, 25 ml. of dry dichloromethane and 5 crystals of p-toluenesulfonic acid monohydrate was stirred for 48 hours and then concentrated in vacuo. The residue was percolated through a 85×100 mm bed of hydrated magnesium silicate, eluting with chloroform to give 3.5 g. of the orange colored compound of formula (30): m.p. 160°–163° C., after crystallization from methyl-cyclohexane; IR (KBr) 3310, 1745, 1640–1540, 1425, 1370, 1235–1225, 1160, 1020, 985 and 870–840 cm$^{-1}$.

EXAMPLE 17

(±)-8α-Ethynyl-6,7,8,9-tetrahydro-5,8β,10-trihydroxy-1,3-dimethyl-6α-trimethylsilyl-anthra-[2,3-c]furan-4,11-dione-8-acetate A mixture of 2.35 g. of (±)-8α-ethynyl-5aβ,6,7,8,9-,9aβ-hexahydro-4,8β,11-trihydroxy-1,3-dimethyl-6α-trimethylsilyl-anthra[2,3-c]furan-5,10-dione-8-acetate (formula 30), 2.80 g. of 94% lead tetraacetate and 25 ml. of glacial acetic acid was ground in a mortar and quenched with 5 ml. of ethylene glycol. The mixture was diluted with 200 ml. of water and extracted up with dichloromethane. The extracts were washed with water, 5% sodium bicarbonate, and brine, then dried over anhydrous sodium sulfate, giving an oil. This oil was combined with 490 mg. of anhydrous potassium acetate in 40 ml. of glacial acetic acid and heated at 95° C., under argon, for 30 minutes, then quenched with 200 ml. of water. Workup as described above and purification on a 68×50 mm bed of hydrated magnesium silicate by eluting with dichloromethane gave an orange-red oil which was crystallized from dichloromethane-methylcyclohexane, giving 1.15 g. of the compound of formula (31): m.p. 236.5°–237° C.; IR (KBr) 1750, 1640, 1605, 1460, 1400, 1250–1200, 1020 and 845 cm$^{-1}$; $^1$H NMR (CDCl$_3$, 90 MHz) δ 0.06 (s, 9H, (CH$_3$)$_3$Si), 2.06 (s, 3H, CH$_3$CO$_2$), 2.06 (dd, 1H, J=12.0 and 9.0 Hz, 7-H$_a$), 2.32 (s, 1H, ≡CH), 2.60 (m, 1H, 7-H$_b$), 2.61 (s, 6H, CH$_3$), 2.83 (d, 1H, J=18.0 Hz, 9-H$_a$), 3.00 (m, 1H, 6-H), 3.70 (dd, 1H, J=18.0 and 1.7 Hz, 9-H$_b$), 13.38 (s, 1H, phenolic OH), and 13.55 (s, 1H, phenolic OH). Calc'd. for C$_{25}$H$_{26}$O$_7$Si: C, 64.36; H, 5.62; O, 24.00; Si, 6.02. Found: C, 64.01; H, 5.52.

EXAMPLE 18

(±)-8α-Ethynyl-6,7,8,9-tetrahydro-5,6β,8β,10-tetrahydroxy-1,3-dimethyl-anthra[2,3-c]furan-4,11-dione-6,8-diacetate A vigorously stirred suspension of 1.0 g. of (±)-8α-ethynyl-6,7,8,9-tetrahydro-5,8β,10-trihydroxy-1,3-dimethyl-6α-trimethylsilyl-anthra[2,3-c]furan-4,11-dione-8-acetate (formula 31), 3.0 g. of lead tetraacetate and 30 ml. of glacial acetic acid was kept at 25° C. for one hour and then 2.0 g. of anhydrous potassium fluoride was added. After 36 hours at 25° C., the suspension was diluted with 300 ml. of dichloromethane and filtered. The filter cake was washed with dichloromethane and the combined filtrate stirred vigorously with 4.0 g. of sodium bisulfite and 100 ml. of water. This mixture was processed as described in Example 17, giving an oil, which on trituration with ether gave 750 mg. of the orange colored compound of formula (32): m.p. above 250° C.; IR (KBr) 1755, 1640, 1605, 1470–1410, 1365, 1250–1200 and 780 cm$^{-1}$; $^1$H NMR (CDCl$_3$, 90 MHz) δ 1.94 (s, 3H CH$_3$CO$_2$), 2.00 (s, 3H, CH$_3$CO$_2$), 2.18 (dd, 1H, J=15.0 and 5.0 Hz, 7-H$_a$), 2.60 (s, 1H, ≡CH), 2.67 (s, 6H, CH$_3$), 2.88 (d, 1H, J=19.0 Hz, 9-H$_a$), 3.33 (dt, 1H, J=15.0 and 1.75 Hz, 7-H$_b$), 3.67 (dd, 1H, J=19.0 and 1.75 Hz, 9-H$_b$), 6.29 (m, 1H, J=5.0 and 1.75 Hz, 6-H) and 13.30 (s, 2H, phenolic OH).

Calc'd. for $C_{24}H_{20}O_9$: C, 63.72, 4.46; O, 31.82. Found: C, 63.52; H, 4.52.

EXAMPLE 19

(±)-8α-Acetyl-6,7,8,9-tetrahydro-5,6β,8β,10-tetrahydroxy-1,3-dimethyl-anthra[2,3-c]furan-4,11-dione-6,8-diacetate A mixture of 235 mg. of (±)-8α-ethynyl-6,7,8,9-tetrahydro-5,6β,8β,10-tetrahydroxy-1,3-dimethyl-anthra-[2,3-c]furan-4,11-dione-6,8-diacetate (formula 32), 637 mg. of mercuric acetate and 30 ml. of ethyl acetate-dichloromethane (5:1) was stirred at 40° C. for 60 hours. Hydrogen sulfide was bubbled through the suspension for 5 minutes. The mercury sulfide was removed by filtration, and the filter cake washed with hot chloroform until the washings were colorless. The filtrate was concentrated and crystallized from ethyl acetate, giving 160 mg. of the orange colored compound of formula (33): m.p. 239°-240° C.; IR (KBr) 1750, 1635, 1605, 1365 and 1245-1200 cm$^{-1}$; $^1$H NMR (CDCl$_3$, 80 HMz) δ 2.02 (s, 3H, CH$_3$CO$_2$), 2.05 (s, 3H, CH$_3$CO$_2$), 2.25 (s, 3H, CH$_3$CO), 2.60 (dd, 1H, J=16.0 and 5.5 Hz, 7-H$_a$), 2.66 (d, 1H, J=19.0 Hz, 9-H$_a$), 2.71 (s, 6H, CH$_3$), 2.93 (dt, 1H, J=16.0 and 1.6 Hz, 7-H$_b$), 3.42 (dd, 1H, J=19.0 and 1.6 Hz, 9-H$_b$), 6.42 (dd, 1H, J=5.5. and 1.6 Hz, 6-H), 13.39 (s, 1H, phenolic OH) and 13.40 (s, 1H, phenolic OH); mass spectrum (70 ev) m/e (relative intensity) 470 (M+; 1), 350 (100), and 307 (44). Calc'd. for $C_{24}H_{22}O_{10}$: C, 61.28,; H, 4.71; O, 34.01. Found: C, 61.36; H, 4.69.

EXAMPLE 20

(±)-8α-Acetyl-6,7,8,9-tetrahydro-5,6β,8β,10-tetrahydroxy-1,3-dimethyl-anthra[2,3-c]furan-4,11-dione A suspension of 200 mg. of (±)-8α-acetyl-6,7,8,9-tetrahydro-5,6β,8β,10-tetrahydroxy-1,3-dimethyl-anthra-[2,3-c]furan-4,11-dione-6,8-diacetate (formula 33) in 80 ml. of 38% hydrochloric acid-water-methanol (10:15:75) was heated at reflux under argon for 40 hours. The mixture was cooled, the solvent removed in vacuo, and the residue azeotroped to dryness with benzene, twice. The residue was triturated with ether, giving 125 mg. of the orange colored compound of formula (34): m.p. 165°-170° C.; IR (KBr) 3450, 1725, 1635, 1623, 1460, 1420, 1370, 1315, 1250-1210, 1133, 1100, 1085, 1020, 985, 930 and 850-770 cm$^{-1}$; $^1$H NMR (CDCl$_3$, 80 MHz) δ 2.25-2.35 (m, 2H, 7-H$_2$), 2.42 (s, 3H, CH$_3$CO), 2.72 (s, 6H, CH$_3$), 3.03 (AB quartet, 2H, Δ$\nu$=34 Hz; J=19.0 Hz, 9-H$_2$), 3.70 (m, 1H, 6-OH), 4.51 (s, 1H, 8-OH), 5.30 (m, 1H, 6-H), 13.37 (s, 1H, phenolic OH), and 13.66 (phenolic OH); mass spectrum (70 ev) m/e (relative intensity) 386 (M+, 55), 368 (M-H$_2$O+, 15), 350 (M-2H$_2$O+, 22), 325 (80) and 297 (100). Calc'd. for $C_{20}H_{18}O_8$: C, 62.18; H, 4.69, O, 33.13. Found: C, 61.98, H, 4.75.

EXAMPLE 21

(±)-8α-Acetyl-6,7,8,9-tetrahydro-5,6β,8β,10-tetrahydroxy-1,3-dimethyl-anthra[2,3-c]furan-4,11-dione-6-[2,3,6-trideoxy-4-O-p-nitrobenzoyl-3-(trifluoroacetamido)-α-L-lyxohexopyranoside] and its β-anomer A mixture of 250 mg. (0.65 mmol) of (±)-8α-acetyl-6,7,8,9-tetrahydro-5,6β,8β,10-tetrahydroxy-1,3-dimethyl-anthra[2,3-c]furan-4,11-dione (formula 34), 3.2 g. of pulverized 3 A° molecular sieves, 1.3 g. of pulverized mercuric cyanide, 620 mg. of pulverized mercuric bromide and 60 ml. of dry dichloromethane was stirred at 25° C. for 2 hours. The chlorosugar was prepared by bubbling anhydrous hydrogen chloride into a suspension of 350 mg. (0.65 mmol) of 2,3,6-trideoxy-1,4-di-O-p-nitrobenzoyl-3-trifluoroacetamido-α-L-lyxo-hexopyranoside in 10 ml. of dry dichloromethane at 0° C. for 3 minutes. The p-nitrobenzoic acid was removed by filtration, and the filtrate evaporated. Two one-molar equivalent portions of freshly-prepared chlorosugar in 5 ml. of dry dichloromethane were added at 0 and 20 hours, while the temperature was maintained at 25°-26° C. A 1.3 g. portion of mercuric cyanide, 620 mg. of mercuric bromide and 3.2 g. of 3 A° molecular sieves were added at 20 hours. After 26 hours the mixture was heated at 40° C. for 4 hours, filtered and the filter cake washed with tetrahydrofuran. The combined filtrate and washings were concentrated, then suspended in chloroform and filtered. The filtrate was washed three times with 30% potassium iodide, then with water, and dried, to produce a mixture of the α- and β-anomers as depicted in formula (35). The dried filtrate was purified by preparative tlc [silica gel GF$_{254}$−6×2 mm×20 cm×20 cm, dichloromethane-methanol (99:1)] giving 225 mg. of the α-anomer (least polar band) and 260 mg. of the β-anomer (second band). The alpha isomer was characterized by IR (KBr) 3400, 1725, 1605, 1540, 1260, 1215, 1160, 1115, 1100, 1015, 975, 955, 870, 835 and 715 cm$^{-1}$; $^1$H NMR (CDCl$_3$, 270 MHz) δ 1.28 (d, 3H, J=6.5 Hz, 6'-CH$_3$), 2.05-2.35 (m, 4H, 7- and 2'-CH$_2$'s), 2.43 (s, 3H, CH$_3$CO), 2.69 (s, 3H, CH$_3$), 2.70 (s, 3H, CH$_3$), 2.88 (d, 1H, J=19.0 Hz, 9-H$_a$), 3.20 (d, 1H J=19.0 Hz, 9-H$_b$), 4.26 (s, 1H, 8-OH), 4.47 (q, 1H, J=6.5 Hz, 5'-H), 4.70 (m, 1H, 3'-H), 5.25 (bs, 1H, 6-H), 5.48 (m, 1H, 4'-H), 5.67 (bs, 1H, 1'-H), 6.61 (d, 1H, NH), 8.26-8.28 (m, 4H, aromatic H's), 13.29 (s, 1H, phenolic OH), and 13.60 (s, 1H, phenolic OH). Calc'd. for $C_{35}H_{31}F_3N_2O_{14}$; C, 55.27; H, 4.11; F, 7.50; N. 3.68; O 29.44. Found: C, 55.01; H, 4.04. The beta isomer was characterized by IR (KBr) 3400, 1725, 1605, 1540, 1260, 1215, 1160, 1115, 1100, 1015, 975, 955, 870, 835 and 715 cm$^{-1}$; $^1$H NMR (CDCl$_3$, 270 MHz) δ 1.25 (d, 3H, J=6.5 Hz, 6'-CH$_3$), 2.00-2.35 (m, 4H, 7- and 2'-CH$_2$'s), 2.40 (s, 3H, CH$_3$CO), 2.71 (s, 3H, CH$_3$), 2.74 (s, 3H, CH$_3$), 2.97 (d, 1H, J=19.0 Hz, 9-H$_a$), 3.27 (d, 1H, J=19.0 Hz, 9-H$_b$), 4.47 (s, 1H, 8-OH), 4.60 (m, 1H, 3'-H), 4.75 (q, 1H, 5'-H), 5.39 (m, 1H, 4'-H), 5.47 (dd, 1H, J=12.5 and 2.0 Hz, 1'-H), 5.55 (bs, 1H, 6-H), 6.45 (d, 1H, NH), 8.27-8.30 (m, 4H, aromatic H's), 13.37 (s, 1H, phenolic OH) and 13.83 (s, 1H, phenolic OH). Calc'd. for $C_{35}H_{31}F_3N_2O_{14}$: C, 55.27; H, 4.11; F, 7.50; N, 3.68; O, 29.44. Found: C, 55.35; H, 4.18.

EXAMPLE 22

(±)-8α-Acetyl-6,7,8,9-tetrahydro-5,6β,8β,10-tetrahydroxy-1,3-dimethyl-anthra[2,3-c]furan-4,11-dione-6-(3-amino-2,3,6-trideoxy-α-L-lyxo-hexopyranoside)-hydrochloride A cold (0° C.) solution of 190 mg. of (±)-8α-acetyl-6,7,8,9-tetrahydro-5,6β,8β,10-tetrahydroxy-1,3-dimethyl-anthra[2,3-c]furan-4,11-dione-6-[2,3,6-trideoxy-4-O-p-nitrobenzoyl-3-(2,2,2-trifluoroacetamido)-α-L-lyxo-hexopyranoside] (formula 35, α-anomer) in 20 ml. of tetrahydrofuran was stirred, under argon, as 20 ml. of cold 0.1N sodium hydroxide was added. The solution was stirred at 0° C. for 4 hours and acidified with 0.1N hydrochloric acid to pH 6. The tetrahydrofuran was evaporated and the solution filtered. The filtrate was diluted with 25 ml. of water and basified with 0.1N sodium hydroxide to a pH of 8.95. The solution was extracted twice with chloroform. The aqueous layer was readjusted to a pH of 10 and reextracted twice with chloroform. The four organic extracts were combined, partitioned with 50 ml. of saturated sodium bicarbonate, water and then dried. Concentration in vacuo produced the free base (of formula 11A) as a foam, which was then dissolved in 15 ml. of chloroform, and 200 μl. of 0.65M ethanolic hydrogen chloride was added at 25° C. The solution was concentrated in vacuo and the residue suspended in anhydrous ether. Cooling to 0° C. gave 35 mg. of the hydrochloride complex of the α-anomer (formula 11A depicts the α-anomer without HCl): IR (KBr) 1715, 1630, 1605, 1450, 1405, 1360, 1295, 1110, 1010, 975, and 820 cm$^{-1}$. Calc'd. for $C_{26}H_{29}NO_{10}.HCl.0.6H_2O$: C, 55.49; H, 5.59; Cl; 6.31; N, 2.49; O, 30.12. Found: C, 55.32; H, 5.80; N, 2.62.

EXAMPLE 23

(±)-8α-Acetyl-6,7,8,9-tetrahydro-5,6β,8β,10-tetrahydroxy-1,3-dimethyl-anthra[2,3-c]furan-4,11-dione-6-(3-amino-2,3,6-trideoxy-β-L-lyxo-hexopyranoside)-hydrochloride Utilizing the same procedure as in Example 22, 200 mg. of the β-anomer of Example 21 gave 32 mg. of the hydrochloride complex of the β-anomer (formula 11B depicts the β-anomer without HCl): IR (KBr) 1715, 1630, 1605, 1450, 1405, 1360, 1295, 1110, 1010, 975, and 820 cm$^{-1}$. Calc'd. for $C_{26}H_{29}NO_{10}.HCl.0.6H_2O$; C, 55.49; H, 5.59; Cl; 6.31; N, 2.49: O, 30.12. Found: C, 55.54; H, 5.77; N, 2.54.

Having thus described the invention, what is claimed is:

1. A compound of the formula

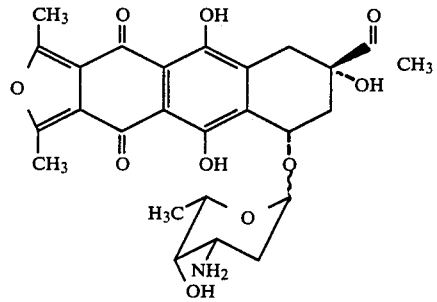

including the individual α- and β-anomers and the hydrochloride complexes thereof.

2. The compound of claim 1 which is (±)-8α-acetyl-6,7,8,9-tetrahydro-5,6β,8β,10-tetrahydroxy-1,3-dimethyl-anthra-[2,3-c]furan-4,11-dione-6-(3-amino-2,3,6-trideoxy-β-L-lyxo-hexopyranoside).

3. The compound of claim 1 which is (±)-8α-acetyl-6,7,8,9-tetrahydro-5,6β,8β,10-tetrahydroxy-1,3-dimethyl-anthra-[2,3-c]furan-4,11-dione-6-(3-amino-2,3,6-trideoxy-α-L-lyxo-hexopyranoside).

4. The compound of claim 3 which is the hydrochloride complex.

5. The compound (±)-8α-acetyl-6,7,8,9-tetrahydro-5,6β,8β,10-tetrahydroxy-1,3-dimethyl-anthra[2,3-c]furan-4,11-dione-6-[2,3,6-trideoxy-4-O-p-nitrobenzoyl-3-(trifluoroacetamido)-α-L-lyxo-hexopyranoside].

6. The compound (±)-8α-acetyl-6,7,8,9-tetrahydro-5,6β,8β,10-tetrahydroxy-1,3-dimethyl-anthra[2,3-c]furan-4,11-dione 6-[2,3,6-trideoxy-4-O-p-nitrobenzoyl-3-(trifluoroacetamido)-β-L-lyxo-hexopyranoside].

7. A therapeutic method for the treatment of a tumor, which comprises administering to a mammal a therapeutically effective non-toxic amount of a compound of claim 1.

8. The method of claim 7 in which said compound is a hydrochloride complex.

* * * * *